United States Patent [19]

Bringhurst et al.

[11] Plant 4,488

[45] Nov. 20, 1979

[54] STRAWBERRY PLANT

[75] Inventors: Royce S. Bringhurst, Davis; Victor Voth, Santa Ana, both of Calif.

[73] Assignee: The Regents of the University of California, Berkeley, Calif.

[21] Appl. No.: 953,816

[22] Filed: Oct. 23, 1978

[51] Int. Cl.[2] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A new and distinct variety of strawberry plant of a short-day type characterized by its best performance in the Watsonville, California, area where yields are equal to or greater than the heavy yielding California cultivars Tioga, Tufts and Aiko on both summer and winter plantings. The variety is also characterized by its ability to crop in mid to late summer with successive crops of fruit on summer and winter plantings. The plants are vigorous and good runner makers and commence flowering later than Tioga or Tufts and about at the same time as Aiko. The fruit is medium to broad conic tending much to wedged coxcomb with unsightly protrusions on summer fruit. Fruit averages as large as Tufts and is as firm and durable as Tioga, Tufts and Aiko. Fruit flavor is equal to or better than the best California cultivars. Shipping and processing is adequate.

3 Drawing Figures

This invention relates to a new and distinctive short-day type strawberry cultivar designated as C52 which is the result of a cross between "Tufts" (U.S. Plant Pat. No. 3561) and Cal 63.7-101 (not patented).

C52 first fruited at the Wolfskill Experimental Orchards of the University of California near Davis in 1974 where it was selected and designated originally a Ca. 72.271-105.

C52 has since been tested with favorable results and asexually reproduced by runners at various University of California Field Stations and facilities and has also been favorably tested in a limited way in representative growers' fields under strict control. Meristem originated virus negative stock for asexual reproduction is under development at the University of California.

FIG. 1 of the accompanying photographic color reproductions shows typical growth, flowering and fruiting characteristics.

Figure 1:
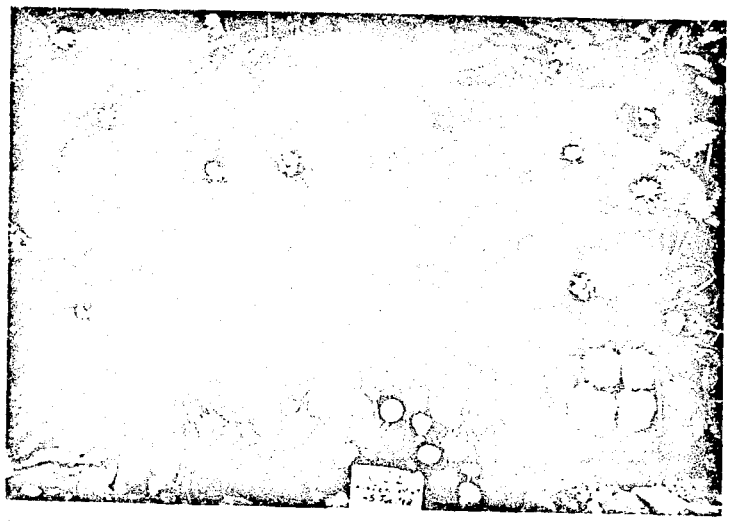
Figure 2:
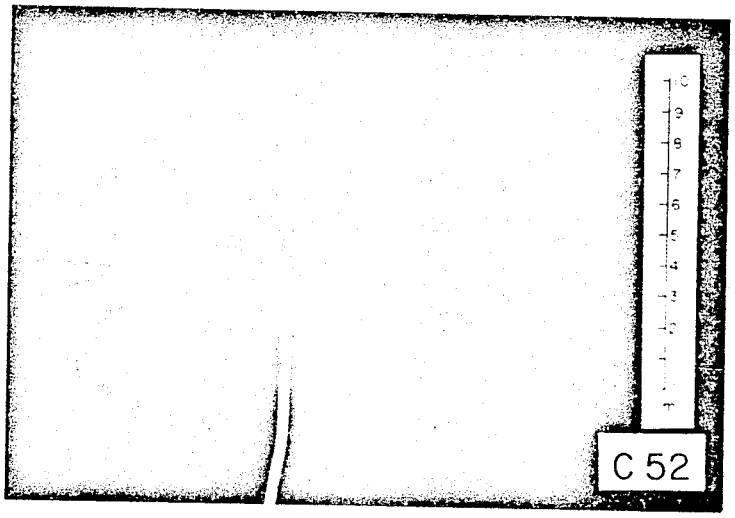
FIG. 2 shows a typical mid-summer mature leaf from a winter planted plant.
Figure 3:
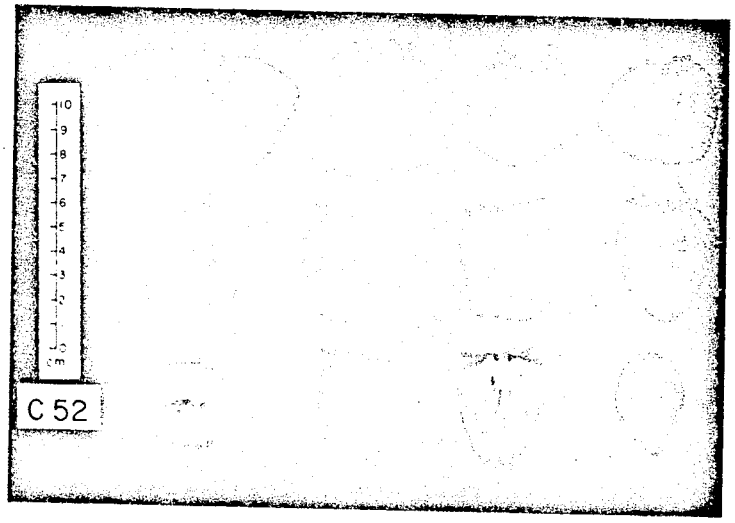
FIG. 3 shows representative mid-season fruit of C52 with longitudinal and cross section views.

C52 has performed best in the Watsonville area where it has yielded as much or more than heavy yielding California cultivars "Tioga" (not patented), "Tufts" and"Aiko" (U.S. Plant Pat. No. 3,981) on summer and winter plantings. It is comparable to "Aiko" in ability to crop in mid to late summer, yielding successive crops of fruit on summer and winter plantings.

The distinctive characteristics of this new strawberry cultivar described in detail below were observed upon its discovery and/or through the test period.

DESCRIPTION

Plants and foliage: C52 plants are erect in growth habit, similar to "Aiko"; medium in size and only slightly larger than those of "Aiko", smaller than "Tioga" or "Tufts". Bract leaves on about 50% of the petioles of winter planted plants and seldom if ever on summer planted plants; much less than "Tioga" or "Tufts" and possibly slightly less than "Aiko". Leaflets are about the same to slightly larger than those of "Tioga" and "Tufts", larger than "Aiko". They are almost the same color as those of "Tioga", about 2.5 GY 4/3 (Munsell Color System–Nickerson Color Fan). The leaflets of C52 tend to have fewer serrations than those of "Tufts" but more than those of "Tioga" and "Aiko" (av of ±11, 12 and 10/half blade, respectively) as averaged over half blades of the 3 leaflets on mid-season mature leaves at Watsonville. The plants are vigorous and C52 is a good runner maker in the nursery with less runners than "Tufts" in fruit plantings.

Isozymes in leaf extracts—Phosphoglucose isomerase (PGI): C52 gave a slow 3 banded pattern similar to that of "Tufts", 30/35 35/35 35/35 35/35 mm, different than the "Tioga" single band or the "Aiko" 5 banded pattern (Scandalios. 1969. Biochem. Genet. 3:3779).

Flowering and flowers: C52 is a standard short-day type that commences flowering about with "Aiko", later than "Tioga" or "Tufts" in all plantings everywhere. Inflorescences are almost as long as those of "Tufts", longer than "Aiko" or "Tioga". The flowers are highly self fertile with ample pollen throughout the season.

Fruit and fruiting: C52 has medium to broad conic somewhat hollow centered fruit, tending very much to a wedged coxcomb with unsightly protrusions on some of the early fruit. The fruit skin color is about the same as that of "Tioga", about 7.5 R 4.5/13 (ibid). The finish is glossy and the flesh color is similar to that of the skin except for a distinctly lighter area near the core. The calyx is medium in size with flush to slightly clasped attachment. The achenes are positioned about flush with the surface to slightly exserted but less so than with "Tufts". The fruit is about as firm and durable as that of "Aiko", "Tioga" and "Tufts" with penetrometer readings of about ± 6.8 vs. " 6.7 for the 3 cultivars at Watsonville. The fruit of C52 has averaged about as large in size as that of "Tufts" in most tests, typically about 20 g/fr.

Fruit quality—Ascorbic acid: C52 averaged ±53 mg/100 g of fresh fruit, greater than "Tioga" (±40) or "Tufts" (±45) and less than "Aiko" (±60) as tested by the method of Loeffler and Ponting. 1942. J. Ind. and Eng. Chem. 14:868. Soluble solids: C52 averaged ±7.8%, not significantly different from "Aiko", "Tioga" or "Tufts" according to our measurements on mid-summer Watsonville fruit. The flavor of C52 is equal to or better than that of the best important California cultivars in our opinion. Some have judged it exceptionally good. As a shipping fruit it is adequate and it should be acceptable for processing.

We claim:

1. The new and distinct variety of strawberry plant herein described and illustrated, and identified by the characteristics enumerated above.

* * * * *